United States Patent [19]

Sabourin et al.

[11] 4,305,751
[45] Dec. 15, 1981

[54] M-ALKYNYLANILIDES AND USE AS HERBICIDES

[75] Inventors: Edward T. Sabourin, Allison Park; Charles M. Selwitz, Monroeville, both of Pa.

[73] Assignee: Gulf Oil Corporation, Pittsburgh, Pa.

[21] Appl. No.: 140,645

[22] Filed: Apr. 16, 1980

[51] Int. Cl.³ ............... A01N 47/30; C07C 127/00
[52] U.S. Cl. ................................. 71/120; 71/106; 71/118; 560/163; 564/52; 564/223
[58] Field of Search ........................ 564/52; 71/120

[56] References Cited

U.S. PATENT DOCUMENTS 3,149,955 9/1964 Fischer et al. .................. 71/120
3,317,600 5/1967 Brooker et al. .................. 71/120
4,046,808 9/1977 Cross .............................. 71/120
4,139,561 2/1979 Onopchenko et al. ........ 564/436

FOREIGN PATENT DOCUMENTS 1280476 2/1961 France ........................... 71/120

Primary Examiner—Glennon H. Hollrah
Attorney, Agent, or Firm—Deane E. Keith; Forrest D. Stine; Carl A. Cline

[57] ABSTRACT

Compounds of the general structural formula,

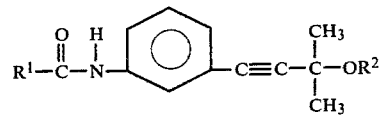

in which $R^1$ is $C_1$ to $C_4$ lower alkyl, cycloalkyl or alkylamino and $R^2$ is H or lower N-alkylcarbamyl are made from corresponding m-aminophenylacetylenic compounds by conventional methods and are useful as selective herbicides.

6 Claims, No Drawings

M-ALKYNYLANILIDES AND USE AS HERBICIDES

DESCRIPTION OF THE INVENTION

This invention is directed to novel compounds of the structural formula

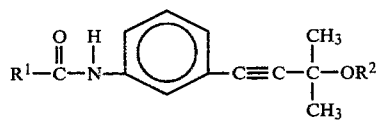

in which $R^1$ is $C_1$ to $C_4$ lower alkyl, cycloalkyl or alkylamino and $R^2$ is H or lower N-alkylcarbamyl and use of these compounds as selective herbicides to combat unwanted vegetation. The compounds of this invention are particularly useful for control of broadleaf weeds in peanuts, by either pre- or post-emergent application. The novel herbicides are characterized by high potency with low residual effects.

SYNTHESIS OF THE HERBICIDES

The compounds of this invention are readily synthesized by reaction of acyl halides with corresponding m-aminophenylacetylenic compounds. The latter compounds may be prepared by methods disclosed in U.S. Pat. No. 4,139,561. Representative procedures are presented in the following illustrative examples.

EXAMPLE 1

Preparation of compound No. 755

This is illustrative of preparations wherein both amine and hydroxy functions are reacted with isocyanate.

To a 500 ml rb flask equipped with a magnetic stirrer, condenser, and a heating mantle were added 2-methyl-4-(3-aminophenyl) 3-butyn-2-ol (7.0 g, 0.040 mole), toluene (200 ml), methylisocyanate (6.8 g, 0.12 mole) and one drop of stannous octanoate. The mixture was brought to reflux for 2 hours, filtered while warm, and allowed to cool overnight. The white, crystalline product was filtered and dried to give 8.6 g, mp 168°–9° C.

EXAMPLE 2

Preparation of compound No. 2499

This is illustrative of preparations wherein only the amine group is reacted with isocyanate.

To a 300 ml rb flask equipped with a magnetic stirrer and a condenser protected with a drying tube were added 2-methyl-4-(3-aminophenyl)-3-butyn-2-ol (8.75 g, 0.050 mole) tetrahydrofuran (100 ml), methylisocyanate (2.90 g, 0.051 mole). The mixture was stirred at room temperature overnight. The solvent was stripped under reduced pressure to give an oil. Trituration with methylene chloride produced a white solid, 10.6 g, mp 150-2 d. The solid was dissolved in warm methanol (50 ml). Water was added until turbid (~30 ml). Upon cooling white needles formed, 10.0 g. The melting point remained at 150°–2° C. with gas evolution.

EXAMPLE 3

Preparation of compound No. 760

This is illustrative of preparations wherein the amine function is converted to an amide.

To a 500 ml Erlenmeyer flask equipped with a magnetic stirrer were charged 2-methyl-4-(3-aminophenyl)-3-butyn-2-ol (10.0 g, 0.057 mole), tetrahydrofuran (150 ml), and triethylamine (6 ml). Propionyl chloride (6 ml) was added and the mixture was stirred at ambient temperature for 30 minutes. After filtration, the filtrate was poured into water (500 ml) and extracted with chloroform (3 × 100 ml). The extracts were dried over magnesium sulfate, filtered, and stripped. The resulting oil was taken up in 50 mls warm toluene. Upon cooling, crystals were filtered and dried, 9.3 g, mp 155°–6° C.

Below are listed compounds of the above general formula which have been synthesized by means of the illustrative procedures.

| Compound No. | $R^1$ | $R^2$ | mp °C. | Recrystallization Solvent |
|---|---|---|---|---|
| 755 | CH$_3$NH— | CH$_3$NHCO | 168–169 | toluene |
| 760 | CH$_3$CH$_2$— | H | 155–156 | toluene |
| 1539 | cyclopropyl | H | 171–171.5 | dichloromethane |
| 1540 | (CH$_3$)$_3$C— | H | 129.5–130.5 | toluene |
| 1547 | (CH$_3$)$_2$CHNH— | (CH$_3$)$_2$CHNHCO— | paste | — |
| 2499 | CH$_3$NH— | H | 150–152 | aq. methanol |
| 2500 | (CH$_3$)$_3$CNH— | H | 158–160 | dichloromethane |

The elemental analyses for the compounds listed above are as follows:

| Compound No. | Analysis Cal. | | | Found | | |
|---|---|---|---|---|---|---|
| | C | H | N | C | H | N |
| 755 | 62.26 | 6.52 | 14.52 | 62.42 | 6.51 | 14.02 |
| 760 | 72.70 | 7.41 | 6.06 | 72.49 | 7.38 | 5.85 |
| 1539 | 74.05 | 7.04 | 5.76 | 74.11 | 7.20 | 5.72 |
| 1540 | 74.10 | 8.16 | 5.40 | 74.79 | 8.26 | 5.18 |
| 2499 | 67.22 | 6.94 | 12.06 | 66.86 | 6.64 | 11.68 |
| 2500 | 70.04 | 8.08 | 10.21 | 70.73 | 7.96 | 9.67 |

A positive identification of molecular structure was obtained by means of nuclear magnetic resonance spectra. These data for the listed compounds appear below.

| | | Nuclear Magnetic Resonance Data |
|---|---|---|
| No. | Solvent | Chemical Shift Relative to Tetramethylsilane (δ) |
| 755 | DMSO-d6 | 1.62(s,6,C(CH$_3$)$_2$); 2.4–2.6(overlapping doublets,6,NHCH$_3$); 3.3(s,1,CH$_3$NHCOO) 6.0(s,1,CH$_3$NHCON); 6.8–7.7(m,4,ArH); 8.6 (s,1,ArNH) |
| 760 | Acetone-d6 | 1.20(t,3,CH$_3$CH$_2$,J=8); 1.58(s,6,C(CH$_3$)$_2$); 2.2(q,2,CH$_3$CH$_2$,J=8); 2.9(s,1,OH); 4.2(s,1,NH); 7.0–7.8(m,4,ArH) |
| 1539 | Acetone-d6 | 0.6–0.9(m,5,C$_3$H$_5$); 1.53(s,6,C(CH$_3$)$_2$); 3.0(s,1,OH); 4.92(s,1,NH); 6.9–7.9 (m,4,ArH) |
| 1540 | Acetone-d6 | 1.30(s,9,C(CH$_3$)$_3$); 1.56(s,6,C(CH$_3$)$_2$); 4.4(bs,1,OH); 6.9–7.9(m,4,ArH); 8.6(bs,1,ArNH) |

-continued

Nuclear Magnetic Resonance Data

| No. | Solvent | Chemical Shift Relative to Tetramethylsilane ($\delta$) |
|---|---|---|
| 2499 | Acetone-d6 | 1.52(s,6,C(CH$_3$)$_2$); 3.70(d,3,HNCH$_3$); 4.9(s,1,OH); 5.8–6.0(bs,1,HNCH$_3$); 6.8–7.7(m,4,ArH); 8.4(s,1,ArNH) |
| 2500 | Acetone-d6 | 1.35(s,9,NH(CH$_3$)$_3$); 1.52(s,6,C(CH$_3$)$_2$); 3.00(s,1,OH); 4.40(s,1,HNC(CH$_3$)$_3$); 6.6–7.7(m,4,ArH); 7.8(s,1,ArH) |
| 1547 | CDCl$_3$ | 1.4(d,6,NCH(CH$_3$)$_2$,J=7); 1.6(d,6,COCH(CH$_3$)$_2$, J=7); 1.54(s,6,C(CH$_3$)$_2$); 3.6–4.8(m,4, (CH$_3$)$_2$CHNH); 6.8–7.7(m,5,ArH + ArNH) |

COMBATING UNWANTED VEGETATION

The novel herbicides are effective when used both post- and pre-emergently. There is described below an illustrative procedure for herbicidal use of the compounds under controlled conditions in the greenhouse so as to obtain data on phytotoxic activity and selectivity.

(1) Post-Emergent Use

An aqueous dispersion of each active compound was prepared by combining 0.4 gram of the compound with about 4 ml of a solvent-emulsifier mixture (3 parts of a commercial polyoxyethylated vegetable oil emulsifier, one part xylene, one part kerosene) and then adding water, with stirring, to a final volume of 40 ml.

The 24 species of plants on which each compound was to be tested were planted in disposable plastic pots in a greenhouse. Ten to eighteen days after emergence of the plants, three pots of each species were sprayed at each rate with an aqueous dispersion of the active compound prepared as described above, at rates of both 1 lb and 3 lb of active compound per acre and at a spray volume of 60 gallons per acre. Approximately one week after the spray application the plants were observed and the results rated according to the following schedule.

DEGREE OF EFFECT

0 = no effect  
1 = slight effect, plants recovered  
2 = moderate effect, injury to 26 to 75 percent of foliage  
3 = severe effect, injury to 76 to 99 percent of foliage  
4 = maximum effect (all plants died)

The same rating schedule was employed to judge pre-emergent results obtained according to the procedure below.

(2) Pre-Emergent Use

A solution of each active compound was prepared by dissolving 290 mg of the compound to be tested in 200 ml of acetone. Disposable paper trays about 2½ inches deep were filled with soil and sprayed with the acetone solution at rates of 3 lb and 1 lb of active chemical per acre of sprayed area, were seeded with 24 species of plant seeds and were then covered with about ¼ inch of soil. Twenty-one days after seeding and treatment the plantings were examined and herbicidal effect was rated.

Results are summarized in the following table.

| Compound No. | | 755 | | 760 | | 1539 | | 1540 | |
|---|---|---|---|---|---|---|---|---|---|
| PLANT SPECIES | Appl'n. Rate (lb./A.) | Pre | Post | Pre | Post | Pre | Post | Pre | Post |
| Xanthium pensylvanicum | 3 | 4 | 4 | | 4 | 4 | 4 | 3 | 4 |
| Cocklebur | 1 | 4 | 4 | 4 | 2 | 4 | 3 | 3 | 3 |
| Chenopodium album | 3 | 4 | 4 | 4 | 4 | 4 | 4 | 4 | 4 |
| Lambsquarters | 1 | 4 | 4 | 4 | 4 | 4 | 4 | 3 | 4 |
| Ipomoea purpurea | 3 | 3 | 4 | 4 | 4 | 4 | 4 | 4 | 4 |
| Morning Glory | 1 | 2 | 3 | 2 | 2 | 4 | 4 | 4 | 4 |
| Amaranthus retroflexus | 3 | 4 | 4 | 4 | 4 | 4 | 4 | 4 | 4 |
| Pigweed | 1 | 4 | 3 | 4 | 4 | 4 | 4 | 3 | 4 |
| Polygonum convolvulus | 3 | 4 | 4 | 4 | 4 | 4 | 4 | 4 | 4 |
| Wild Buckwheat | 1 | 4 | 4 | 4 | 4 | 4 | 3 | 3 | 4 |
| Brassica kaber | 3 | 4 | 4 | 4 | 4 | 4 | 4 | 4 | 4 |
| Wild Mustard | 1 | 4 | 4 | 4 | 4 | 4 | 4 | 4 | 4 |
| Echinochloa crusgalli | 3 | 4 | 4 | 1 | 4 | 3 | 3 | 3 | 2 |
| Barnyard Grass | 1 | 3 | 2 | 1 | 3 | 3 | 3 | 3 | 1 |
| Digitaria sanguinalis | 3 | 3 | 3 | 1 | 1 | 2 | 2 | 2 | 2 |
| Crabgrass | 1 | 0 | 0 | 0 | 0 | 1 | 0 | 0 | 1 |
| Bromus tectorum | 3 | 3 | 3 | 2 | 0 | 2 | 1 | 1 | 2 |
| Downy Brome | 1 | 1 | 0 | 0 | 0 | 1 | 0 | 0 | 0 |
| Setaria faberii | 3 | 4 | 4 | 2 | 2 | 2 | 2 | 3 | 3 |
| Giant Foxtail | 1 | 1 | 1 | 0 | 1 | 3 | 3 | 0 | 2 |
| Setaria viridis | 3 | 4 | 4 | 4 | 4 | 4 | 4 | 4 | 4 |
| Green Foxtail | 1 | 4 | 3 | 3 | 2 | 3 | 2 | 2 | 2 |
| Cyperus esculentis | 3 | 0 | 0 | 0 | 0 | 0 | 0 | 0 | 0 |
| Nutsedge | 1 | 0 | 0 | 0 | 0 | 0 | 0 | 0 | 0 |
| Sorghum bicolor | 3 | 4 | 3 | 0 | 3 | 2 | 3 | 3 | 3 |
| Shatter Cane | 1 | 2 | 1 | 0 | 2 | 3 | 3 | 3 | 1 |
| Avena fatua | 3 | 4 | 4 | 4 | 4 | 3 | 3 | 3 | 3 |
| Wild Oats | 1 | 4 | 4 | 1 | 3 | 2 | 1 | 1 | 2 |
| Medicago sativa | 3 | 4 | 4 | 4 | 4 | 4 | 3 | 3 | 4 |
| Alfalfa | 1 | 1 | 4 | 3 | 1 | 4 | 4 | 1 | 2 |
| Gossypium herbaceum | 3 | 3 | 4 | 3 | 2 | 4 | 4 | 4 | 4 |
| Cotton | 1 | 1 | 2 | 2 | 1 | 3 | 3 | 1 | 4 |
| Arachis hypogaea | 3 | 2 | 3 | 3 | 0 | 1 | 1 | 1 | 2 |
| Peanut | 1 | 0 | 1 | 1 | 0 | 1 | 1 | 0 | 1 |
| Soja max | 3 | 4 | 4 | 4 | 4 | 4 | 4 | 3 | 3 |
| Soybean | 1 | 4 | 3 | 3 | 3 | 3 | 3 | 1 | 2 |
| Beta vulgaris | 3 | 4 | 4 | 4 | 4 | 4 | 4 | 4 | 4 |
| Sugar Beets | 1 | 4 | 4 | 4 | 4 | 4 | 4 | 4 | 4 |
| Lycopersicum exculentum | 3 | 4 | 4 | 4 | 4 | 4 | 4 | 4 | 4 |

| -continued | | | | | | | | |
|---|---|---|---|---|---|---|---|---|
| Tomato | 1 | 4 | 4 | 4 | 4 | 4 | 4 | 4 |
| Zea mays | 3 | 3 | 1 | 0 | 4 | 3 | 3 | 2 |
| Corn | 1 | 2 | 1 | 0 | 3 | 3 | 2 | 1 |
| Sorghum vulgare | 3 | 4 | 3 | 0 | 3 | 2 | 3 | 2 |
| Grain Sorghum | 1 | 2 | 1 | 0 | 2 | 3 | 3 | 1 |
| Oryza sativa | 3 | 4 | 4 | 2 | — | — | — | — |
| Rice | 1 | 4 | 4 | 1 | 2 | — | — | — |
| Triticum aestivum | 3 | 4 | 4 | 3 | 4 | 3 | 4 | 3 |
| Wheat | 1 | 4 | 3 | 2 | 2 | 2 | 3 | 2 |

| Compound No. | | 1547 | | 2499 | | 2500 | |
|---|---|---|---|---|---|---|---|
| PLANT SPECIES | Appl'n. Rate (lb./A.) | Pre | Post | Pre | Post | Pre | Post |
| Xanthium pensylvanicum | 3 | 4 | 4 | 4 | 4 | 4 | 4 |
| Cocklebur | 1 | 3 | 4 | 4 | 4 | 3 | — |
| Chenopodium album | 3 | 4 | 4 | 4 | 4 | 4 | 4 |
| Lambsquarters | 1 | 4 | 4 | 4 | 4 | 4 | 4 |
| Ipomoea purpurea | 3 | 3 | 4 | 4 | 4 | 4 | 4 |
| Morning Glory | 1 | 4 | 4 | 3 | 4 | 2 | 2 |
| Amaranthus retroflexus | 3 | 4 | 4 | 4 | 4 | 4 | 4 |
| Pigweed | 1 | 2 | 4 | 4 | 4 | 4 | 4 |
| Polygonum convolvulus | 3 | 4 | 4 | 4 | 4 | 4 | 4 |
| Wild Buckwheat | 1 | 3 | 4 | 4 | 4 | 4 | 4 |
| Brassica kaber | 3 | 4 | 4 | 4 | 4 | 4 | 4 |
| Wild Mustard | 1 | 1 | 4 | 4 | 4 | 4 | 4 |
| Echinochloa crusgalli | 3 | 4 | 3 | 4 | 4 | 4 | 4 |
| Barnyard Grass | 1 | 3 | 1 | 4 | 4 | 4 | 4 |
| Digitaria sanguinalis | 3 | 2 | 1 | 4 | 4 | 4 | 4 |
| Crabgrass | 1 | 0 | 0 | 3 | 4 | 4 | 4 |
| Bromus tectorum | 3 | 1 | 2 | 4 | 4 | 4 | 4 |
| Downy Brome | 1 | 0 | 0 | 3 | 4 | 2 | 3 |
| Setaria faberii | 3 | 2 | 2 | 4 | 4 | 4 | 4 |
| Giant Foxtail | 1 | 1 | 1 | 3 | 4 | 2 | 3 |
| Setaria viridis | 3 | 4 | 3 | 4 | 4 | 4 | 4 |
| Green Foxtail | 1 | 2 | 1 | 4 | 4 | 4 | 4 |
| Cyperus esculentis | 3 | 0 | 0 | 1 | 1 | 1 | 1 |
| Nutsedge | 1 | 0 | 0 | 0 | 0 | 0 | 0 |
| Sorghum bicolor | 3 | 3 | 2 | 3 | 3 | 4 | 3 |
| Shatter Cane | 1 | 2 | 0 | 3 | 3 | 3 | 3 |
| Avenua fatua | 3 | 4 | 4 | 4 | 4 | 4 | 4 |
| Wild Oats | 1 | 2 | 2 | 4 | 4 | 4 | 4 |
| Medicago sativa | 3 | 3 | 4 | 4 | 4 | 4 | 4 |
| Alfalfa | 1 | 0 | 2 | 4 | 4 | 4 | 4 |
| Gossypium herbaceum | 3 | 3 | 4 | 4 | 4 | 4 | 4 |
| Cotton | 1 | 0 | 2 | 2 | 4 | 1 | 4 |
| Arachis hypogaea | 3 | 0 | 3 | 1 | 3 | 1 | — |
| Peanut | 1 | 0 | 1 | 0 | 3 | 0 | 1 |
| Soja max | 3 | 4 | 2 | 4 | 4 | 4 | 4 |
| Soybean | 1 | 3 | 2 | 4 | 4 | 3 | 4 |
| Beta vulgaris | 3 | 4 | 4 | 4 | 4 | 4 | 4 |
| Sugar Beets | 1 | 2 | 4 | 4 | 4 | 4 | 4 |
| Lycopersicum esculentum | 3 | 4 | 4 | 4 | 4 | 4 | 4 |
| Tomato | 1 | 3 | 4 | 4 | 4 | 4 | 4 |
| Zea mays | 3 | 3 | 2 | 4 | 4 | 4 | 4 |
| Corn | 1 | 3 | 0 | 4 | 3 | 4 | 3 |
| Sorghum vulgare | 3 | 4 | 2 | 4 | 4 | 4 | 4 |
| Grain Sorghum | 1 | 2 | 0 | 3 | 3 | 4 | 3 |
| Oryza sativa | 3 | — | — | 3 | 4 | 3 | 4 |
| Rice | 1 | — | — | 3 | 4 | 3 | 4 |
| Triticum aestivum | 3 | 3 | 3 | 4 | 4 | 4 | 4 |
| Wheat | 1 | 3 | 1 | 4 | 4 | 4 | 4 |

The information presented in tabular form herein will enable a worker in the art to make a selection from among the herbicidal compounds of the invention and to make some judgement with regard to application rates, depending upon the species which it is desired to control.

The compounds are usually applied in combination with inert carriers or diluents, as in aqueous sprays, granules and dust formulations in accordance with established practice in the art. An aqueous spray is usually prepared by mixing a wettable powder or emulsifiable concentrate formulation of a herbicide with a relatively large amount of water to form a dispersion.

Wettable powders comprise intimate, finely divided mixtures of active compounds, inert solid carriers and surface active agents. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to about 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates of the herbicidal compounds comprise in each instance, a solution of active compound in a liquid carrier which is a mixture of water-immiscible solvent and surfactants, including emulsifiers. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

In general, the herbicidal compounds are applied in formulations which desirably contain from 0.1 percent to 95 percent by weight of a compound of formula (1) and from 0.1 to 75 percent by weight of a carrier or surfactant.

When a compound is to be applied to the soil, as for a pre-emergence application, granular formulations are sometimes more convenient than sprays. A typical granular formulation comprises the active compound dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound is sprayed on the granules while they are being agitated in a suitable mixing apparatus, after which the granules are dried with a current of air during continued agitation.

I claim:

1. Compounds having the general structural formula

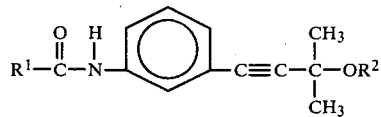

in which $R^1$ is $C_1$ to $C_4$ lower alkylamino and $R^2$ is H.

2. An agricultural composition comprising from 0.1 percent to 95 percent by weight of a compound of claim 1 and from 0.1 to 75 percent by weight of a carrier or surfactant.

3. The method of combating unwanted vegetation comprising applying to said vegetation either pre- or post-emergently an effective amount of a compound of claim 1 in combination with an inert carrier.

4. The method of claim 3 in which unwanted vegetation is combated in the presence of peanuts.

5. The compound of claim 1 in which $R^1$ is methylamino and $R^2$ is hydrogen.

6. The compound of claim 1 in which $R^1$ is tert. butylamino and $R^2$ is hydrogen.

* * * * *